(12) United States Patent
Zapalac

(10) Patent No.: US 6,789,943 B2
(45) Date of Patent: Sep. 14, 2004

(54) METHOD AND APPARATUS FOR SCATTER MEASUREMENT USING AN OCCLUDED DETECTOR RING

(75) Inventor: Geordie Henry Zapalac, Grass Valley, CA (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/292,985

(22) Filed: Nov. 12, 2002

(65) Prior Publication Data

US 2004/0091079 A1 May 13, 2004

(51) Int. Cl.[7] ............................................. G01D 18/00
(52) U.S. Cl. ....................................... 378/207; 378/18
(58) Field of Search ............................... 378/207, 98.4, 378/18, 62

(56) References Cited

U.S. PATENT DOCUMENTS

| | | | |
|---|---|---|---|
| 4,126,789 A | * 11/1978 | Vogl et al. | 378/145 |
| 4,352,021 A | 9/1982 | Boyd et al. | 378/12 |
| 4,521,900 A | 6/1985 | Rand | 378/137 |
| 4,521,901 A | 6/1985 | Rand | 378/138 |
| 4,625,150 A | 11/1986 | Rand | 315/111.31 |
| 4,644,168 A | 2/1987 | Rand et al. | 250/398 |
| 4,995,107 A | * 2/1991 | Klingenbeck | 378/7 |
| 5,193,105 A | 3/1993 | Rand et al. | 378/137 |
| 5,289,519 A | 2/1994 | Rand | 378/4 |
| 5,406,479 A | 4/1995 | Harman | 364/413.17 |
| 5,719,914 A | 2/1998 | Rand et al. | 378/4 |
| 6,208,711 B1 | 3/2001 | Rand et al. | 378/138 |

* cited by examiner

Primary Examiner—Craig E. Church
Assistant Examiner—Jurie Yun
(74) Attorney, Agent, or Firm—McAndrews, Held & MAlloy, Ltd.; Peter J. Vogel; Michael A. Dellapenna (57) ABSTRACT

Certain embodiments include a system and method for scatter measurement and correction. The method includes performing a calibration scan using a phantom to measure a scatter signal ratio between scatter x-rays impacting a first detector ring and scatter x-rays impacting a second detector ring. The scatter signal ratio is used to determine a scatter scale factor. The method further includes positioning a collimator such that the first detector ring is occluded from a path of primary x-rays generated by a target. The method also includes executing a low exposure scan to obtain x-ray scatter data using the first detector ring and the second detector ring and applying the scatter scale factor to the scatter data to produce scaled scatter data. The method further includes obtaining image data using the first detector ring and/or the said second detector ring and adjusting the image data using the scaled scatter data.

21 Claims, 5 Drawing Sheets

METHOD AND APPARATUS FOR SCATTER MEASUREMENT USING AN OCCLUDED DETECTOR RING

BACKGROUND OF THE INVENTION

The present invention generally relates to scatter measurement in a diagnostic imaging system. In particular, the present invention relates to measurement and correction of scatter using an occluded detector ring in a multiple ring diagnostic imaging system.

Diagnostic imaging systems encompass a variety of imaging modalities, such as x-ray systems, computerized tomography (CT) systems, ultrasound systems, electron beam tomography (EBT) systems, magnetic resonance (MR) systems, and the like. Diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of items in an object. The information gained from diagnostic imaging has applications in many fields, including medicine and manufacturing.

EBT scanners are generally described in U.S. Pat. No. 4,352,021 to Boyd, et al. (Sep. 28, 1982), and U.S. Pat. Nos. 4,521,900 (Jun. 4, 1985), 4,521,901 (Jun. 4, 1985), 4,625,150 (Nov. 25, 1986), 4,644,168 (Feb. 17, 1987), 5,193,105 (Mar. 9, 1993), 5,289,519 (Feb. 22, 1994), 5,719,914 (Feb. 17, 1998) and 6,208,711 all to Rand, et al., and U.S. Pat. No. 5,406,479 to Harman (Apr. 11, 1995). The above listed patents are referred to and incorporated herein by reference in their entireties.

As described in the above-referenced patents, an electron beam is produced by an electron source at the upstream end of an evacuated, generally conical shaped housing chamber. A large negative potential (e.g. −130 kV or −140 kV) on a cathode of the electron source accelerates the electron beam downstream along an axis of the housing chamber. Further downstream, a beam optical system that includes solenoid, quadrupole, and deflection coils focus and deflect the beam to scan along an x-ray producing target. EBT systems utilize a high energy beam of electrons to strike the target and produce x-rays for irradiating an object to be imaged. The point where the electrons strike the target is called the "beam spot". The final beam spot at the target is smaller than that produced at the electron source, and must be suitably sharp and free of aberrations so as not to degrade definition in the image rendered by the scanner.

The x-rays produced by the target penetrate a patient or other object and are detected by an array of detectors. The detector array, like the target, is coaxial with and defines a plane orthogonal to the scanner axis of symmetry. The output from the detector array is digitized, stored, and computer processed to produce a reconstructed x-ray image of a slice of the object, typically an image of a patient's anatomy such as the heart or lungs.

An EBT scanner allows for the collection of many angles of view and scanning of a number of slices in a short time. There is no mechanically moving gantry. Both high resolution and dynamic scanning modes may be provided while eliminating the need for any target or detector motion by replacing conventional x-ray tubes with electron beam technology.

Multiple views may be generated by magnetically steering a focused electron beam along a 210 degree target ring positioned beneath a subject. Opposite the target ring is a stationary detector ring of Cadmium tungstate crystals encompassing a 216 degree arc above the subject. Photodiodes in the detector ring are used for recording transmitted x-ray intensity. X-ray intensity data may be processed to produce an image.

In order to help ensure that diagnostic images may be used reliably, image correction is advantageous in diagnostic imaging systems. The image correction in diagnostic imaging systems is important for several reasons, including image quality and system performance. Poor image quality may prevent reliable analysis of the image. For example, a decrease in image contrast quality may yield an unreliable image that is not usable clinically. Additionally, the advent of real-time imaging systems has increased the importance of generating clear, high quality images. Inaccuracies or errors in an imaging system may result in blurring, streaking, or introduction of ghost images or artifacts in a resulting image. For example, if electrons are scattered by a bone or other dense component in an object and then impact a detector in the imaging system, artifacts in a scanned image may result. The correction of diagnostic images may help to produce a distinct and usable representation of an object.

Scatter resulting from the diagnostic imaging system or object being imaged creates x-rays that do not original from the x-ray source. Scattered x-rays spuriously increase the signal detected by a detector in an imaging system, particularly if the primary detected signal is highly attenuated (i.e., the detected signal is weakened due to absorption of incident x-rays). When the image is reconstructed with scatter errors, artifacts are present in the image. Artifacts reduce the diagnostic quality of the image.

In order to correct for scatter, a measurement of the scatter is taken and subtracted from the primary signal. Present scatter correction methods subtract the scatter signal from the primary data signal and make many assumptions about the nature of the scatter signal. As a result, significant scatter artifacts remain after scatter correction. Ideally, the scatter would be measured directly so that the scatter could be subtracted without making assumptions.

Thus, a need exists for improving image quality by reducing scatter. A need also exists for a method and apparatus for scatter correction without making assumptions regarding the scattered x-rays.

BRIEF SUMMARY OF THE INVENTION

Certain embodiments include a system and method for scatter measurement and correction. The method includes performing a calibration scan using a phantom to measure a scatter signal ratio between scatter x-rays impacting a first detector ring and scatter x-rays impacting a second detector ring. The scatter signal ratio is used to determine a scatter scale factor. The method further includes positioning the collimator such that the first detector ring is occluded from a path of primary x-rays generated by a target. The method also includes executing a low exposure scan to obtain x-ray scatter data using the first detector ring and applying the scatter scale factor to the scatter data to produce scaled scatter data. The method further includes obtaining image data using the first detector ring and/or the said second detector ring and adjusting the image data using the scaled scatter data.

The phantom may be a water-filled phantom including a bar in an interior portion of the phantom to block x-rays. The image data may be obtained during a 50 ms scan. Additionally, the scaled scatter data may be smoothed using a filter, such as a Gaussian convolution filter. The scaled scatter data may be further scaled for overestimation of x-ray scatter. In a certain embodiment, the adjusting step includes subtracting the scaled scatter data from the image data. In a certain embodiment, the scatter data is obtained during preview scanning by including one full scan for every five preview scans. In another embodiment, scatter data is acquired during a single slice coronary calcium scan.

The system includes first and second detector rings for detecting radiation. The first detector ring is capable of being blocked from a primary path of said radiation. The first detector ring acquires scatter data and at least one of the first detector ring and the second detector ring acquires image data. The system also includes a phantom for use in calibration of a scatter scaling factor for radiation scatter and a processor for reducing scatter in the image data. The processor applies the scatter scaling factor to the scatter data and subtracts the scatter data from the image data.

The system may further include a collimator for controlling the primary path of the radiation. In a certain embodiment, the phantom includes a boundary around an exterior of the phantom, an interior portion of the phantom filled with water, and a bar positioned in the interior portion of the phantom to block radiation. The system may further include a Gaussian convolution filter for smoothing the scatter data. In a certain embodiment, the first and second detector rings include a plurality of detector elements for receiving the radiation. The first and second detector rings may be exposed to a low exposure preview scan to acquire the scatter data. In a certain embodiment, the scatter data is obtained using a series of five low exposure scans and one full scan.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiment of an Electron Beam Tomography (EBT) imaging system. It is understood that the present invention may be used with imaging systems other than EBT imaging systems.

Figure 1:
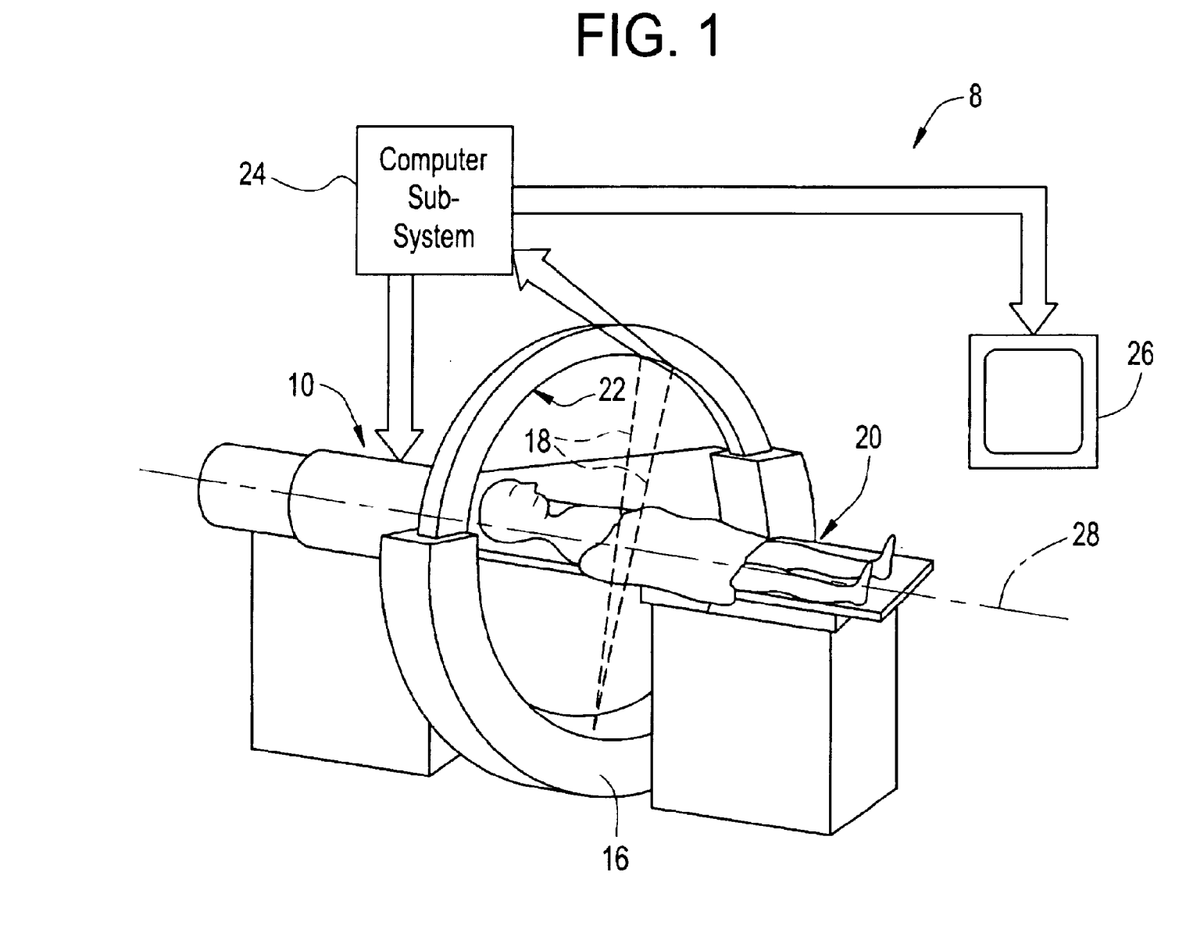
FIG. 1 illustrates an EBT imaging system that is used in accordance with an embodiment of the present invention.
Figure 2:
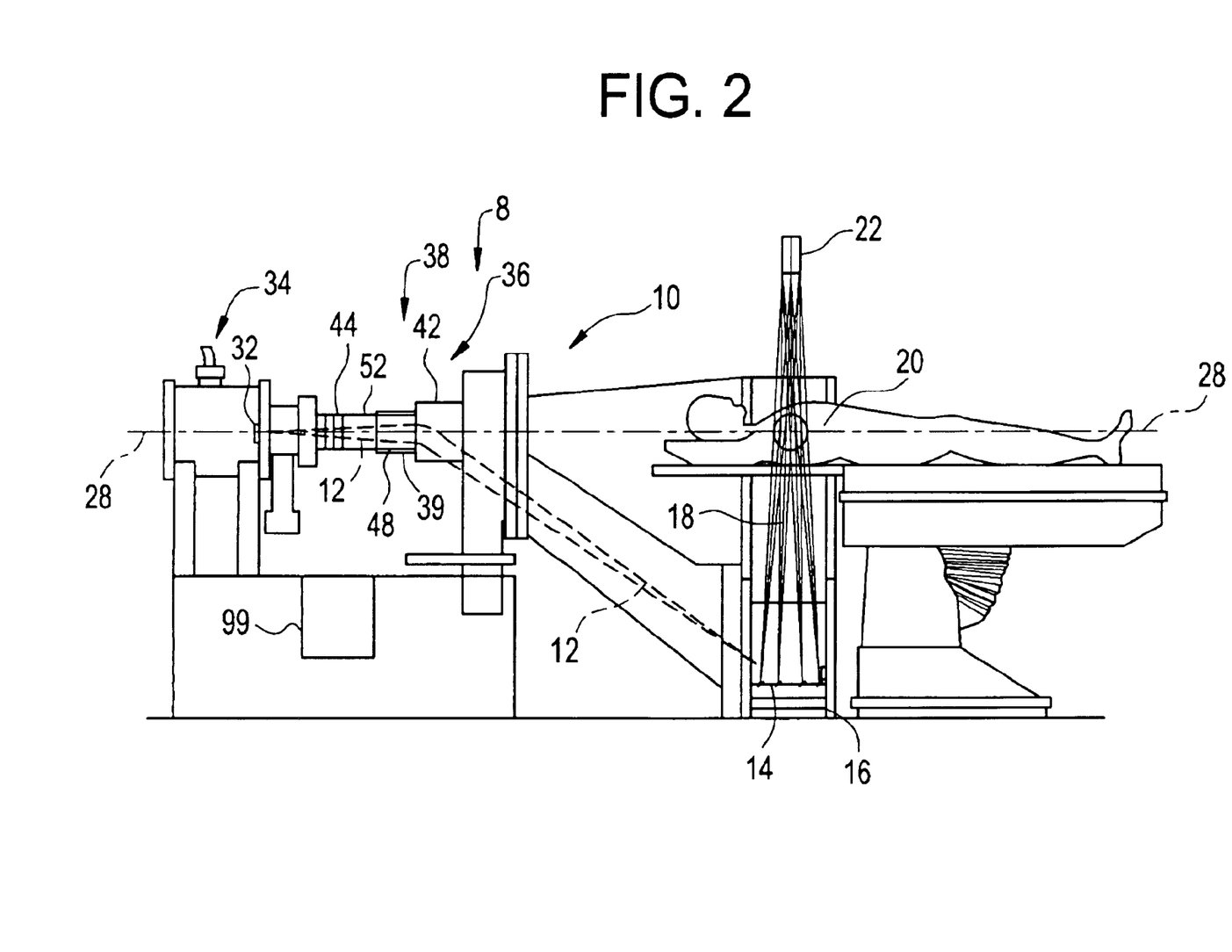
FIG. 2 illustrates a side view of an EBT imaging system, including an electron beam and x-ray emission path in accordance with an embodiment of the present invention.

Before describing certain embodiments of the present invention, it is helpful to understand the operation of an EBT imaging system. FIG. 1 and FIG. 2 illustrate an imaging system 8 formed according to an embodiment of the present invention. As shown in FIG. 2, system 8 includes a vacuum chamber housing 10 in which an electron beam 12 is generated at a cathode of an electron source 32 located in an upstream region 34, in response to a voltage, such as −130 kV. The electron beam 12 is then controlled by an optical system 38, including a magnetic lens 39 and a deflection coil 42, to scan at least one circular target 14 located within a front lower portion 16 of the chamber housing 10.

When scanned by the focused electron beam 12, the target 14 emits a moving fanlike beam of x-rays 18. X-rays 18 then pass through a region of a subject 20 (a patient or other object, for example) and register upon a detector array 22 located diametrically opposite the target 14. Detector data is output to a processor or computer subsystem 24 that processes and records the data, producing an image of a slice of the subject 20 on a video monitor 26. The computer subsystem 24 also controls the system 8 and electron beam production therein.

The beam optical system 38 is mounted within the chamber housing 10 and includes the magnetic lens 39, deflecting coils and quadrupole coils (collectively coils 42), and an electrode assembly 44. The lens 39 and coils 42 contribute a focusing effect to help shape a final beam spot as the electron beam scans one of the targets 14.

The electrode assembly 44 is mounted within the chamber housing 10 between the electron source 32 and the remainder of the beam optical assembly 38 such that the electron beam 12 passes axially through the assembly 44 along the z-axis 28. The z-axis 28 is coaxial with the electron beam 12 upstream from the beam optics assembly 38 within the chamber housing 10. The z-axis 28 also represents the longitudinal axis of the chamber housing 10 and the axis of symmetry for the electrode assembly 44 and the beam optics assembly 38 in accordance with an embodiment of the present invention. The z-axis 28 is also the scanning axis through the subject 20 being scanned.

To scan the subject 20, an x-ray fan beam is rotated in the x-y plane through various positions or fan view angles. The center of the fan beam is rotated through 210 degrees and is detected by an arc of detector elements in the detector array 22. Each detector ring in the detector array 22 may include 1728 cadmium-tungstate crystal detector elements. The fan beam passes through the subject 20 within a reconstruction circle and impinges upon the detector array 22. Data samples obtained by a detector element in the detector array 22 over a single scan of the subject 20 constitute a detector fan. By way of example, the detector fan may include 864 data points or samples for a 50 ms scan. Each sample represents an x-ray path from the target 14 to a detector element that is attenuated by the subject 20. All data samples (all x-ray paths) collected over a scan from all detector elements (all detector fans) constitute a fan view sinogram.

Figure 3:
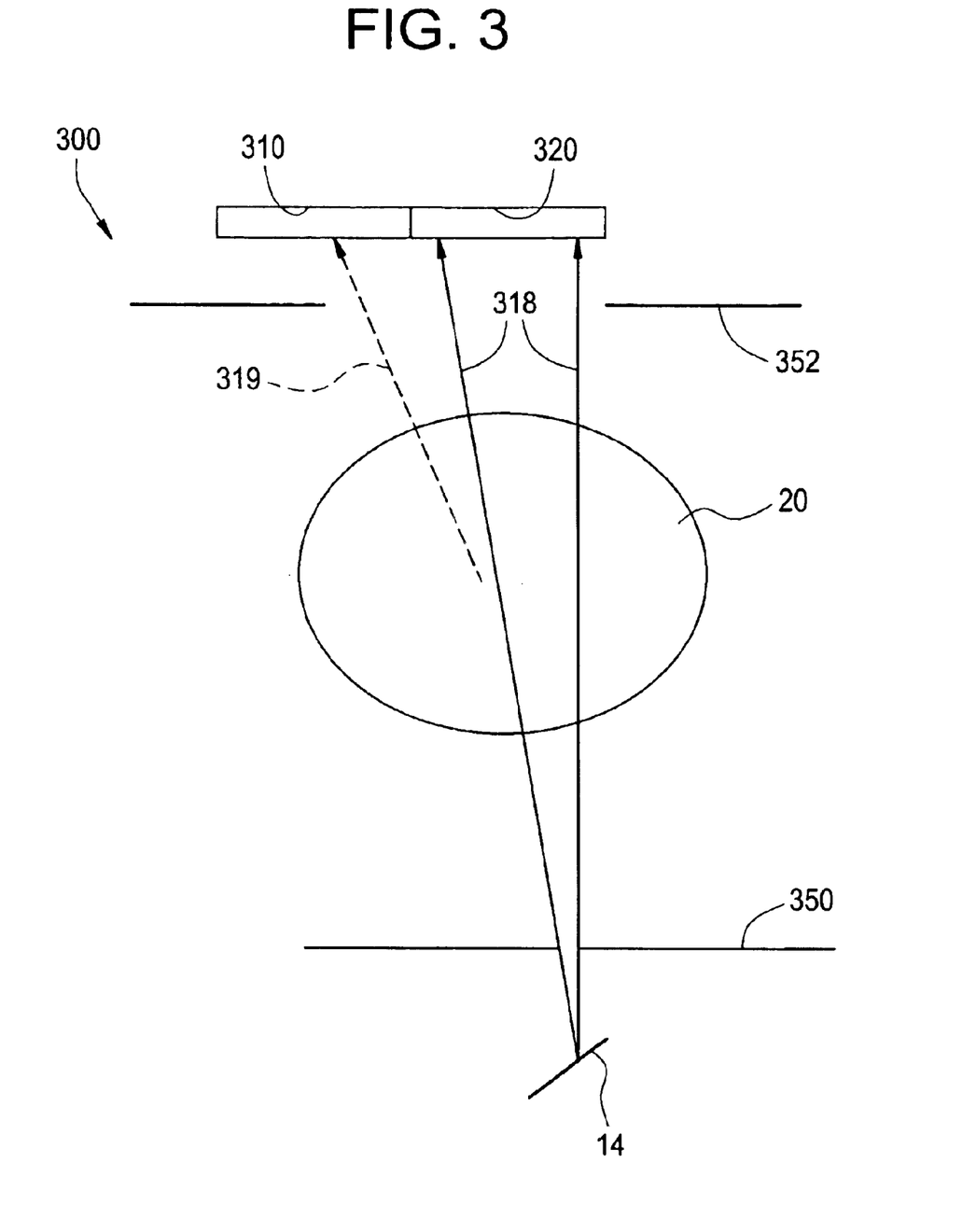
FIG. 3 illustrates a dual ring detector array used in accordance with an embodiment of the present invention.

Although a detector array may include multiple detector rings, a dual ring detector array will be used to illustrate certain embodiments of the present invention. FIG. 3 illustrates a dual ring detector array 300 used in accordance with an embodiment of the present invention. The dual ring detector array 300 may be used as the detector array 22 in the system 8. The detector array 300 includes a first detector ring 310 and a second detector ring 320. Detector rings 310 and 320 are located next to each other and concentric with the z-axis 28 of the system 8 that runs in the direction of a table or support on which the subject 20 is positioned.

If direct x-rays are blocked from detector ring 310, only scattered x-rays 319 will be measured by detector ring 310. All of the primary x-rays 318 that pass collimation (are allowed to pass from the target 14 to the detector array 300) go into the detector ring 320. That is a collimator, such as a collimator having an entrance slit 350 and an exit slit 352, collimates x-rays from the targets 14 into a primary x-ray beam. The collimator 350, 352 controls the width and direction of the primary x-rays 318 from the targets 14 that irradiate the subject 20 as the primary x-rays 318 travel to the detector ring 320. Scanning with one detector ring 320 receiving primary x-rays 318 is known as "single slice mode." Ideally, scatter data obtained at detector ring 310 from the scattered x-rays 319 would be subtracted from the image data containing both scattered x-rays 319 and primary image x-rays 318 at detector ring 320. However, scatter differs between detector rings 310 and 320 due to geometry of the system 8 (detector widths, position of a collimator, etc.). Thus, the system 8 may be calibrated to scale the scatter data of detector ring 310 for use with the image data of detector ring 320.

A phantom may be used with the detector array 300 to calibrate the acceptance of system 8 for scatter at detector rings 310 and 320. As described above, scatter data obtained by detector ring 310 may not be directly subtracted from data obtained by detector ring 320 because the geometric acceptance for scatter for detector ring 310 is different from the acceptance for scatter for detector ring 320. A scale factor may be determined from a ratio of scatter between detector rings 310 and 320. The scale factor may be applied to the scatter data obtained by detector ring 310 before the scatter data is subtracted from the image data obtained by detector ring 320.

Figure 4:
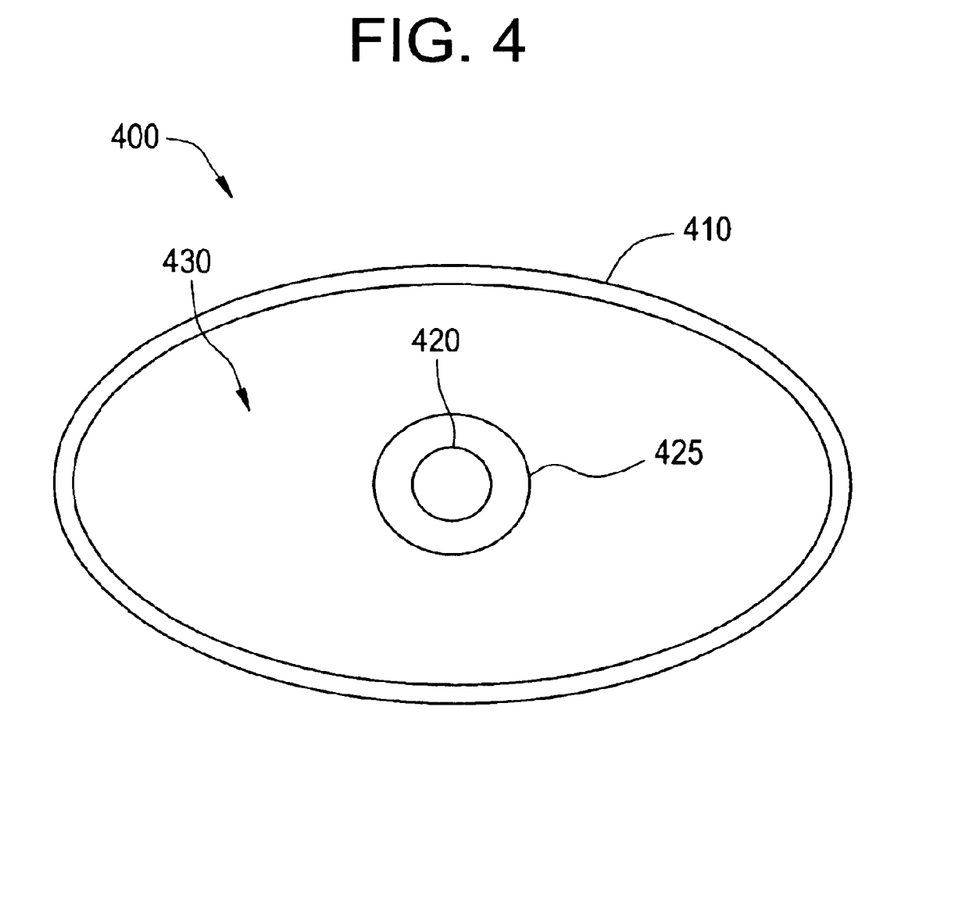
FIG. 4 depicts an object scatter phantom used in accordance with an embodiment of the present invention.

FIG. 4 depicts an object scatter phantom 400 used in accordance with an embodiment of the present invention. The phantom 400 includes an outer border 410, typically made from plastic. In a certain embodiment, the outer border 410 is a plastic ellipse measuring 14 inches by 9 inches. The outer border 410 forms the boundary and outer edge of the phantom 400. The phantom 400 also includes a bar 420, typically a lead bar. In a certain embodiment, the bar 420 is a one-inch diameter lead bar located in the center of the phantom 400. Water 430 fills the phantom 400 inside the outer border 410 and surrounds the bar 420. The phantom 400 may also include an inner border 425 surrounding the bar 420. The inner border 425 allows the bar 420 to be removed without opening the entire phantom 400.

The phantom 400 may be used to measure a ratio of scatter between detector rings 310 and 320. The phantom 400 may be used to measure the ratio of scattered x-rays 319 in both detector rings 310, 320 in single slice mode so that the scatter data from detector ring 310 may be scaled to a scatter correction value that may be subtracted from the image data at detector ring 320. The ratio is an approximate measurement but serves to reduce scatter in the resulting image obtained from the detector ring 320 data.

The phantom 400 roughly imitates a cross-section of a patient. A signal obtained from detector elements behind the bar 420 is measured. The detector elements positioned behind the bar 420 measure only scattered x-rays 319 because the primary x-rays 318 are blocked by the bar 420. Two kinds of scatter are registered in the detector elements. The first is object scatter: x-rays created within the phantom 400 by primary x-rays that enter the phantom 400. The second type of scatter is machine scatter: scattered x-rays that originate from the surfaces of components in the system 8 rather than from the phantom 400. The phantom 400 crudely imitates the scatter from a patient: object scatter is comparable to a patient because the cross section of the phantom 400 is roughly the size of an average adult person, for example, and machine scatter is attenuated (lessened) by the phantom 400 in about the same way that machine scatter is attenuated by a patient. The bar 420 is positioned on the isocenter of the system 8 (in the center of the reconstruction circle) and is concentric to the detector rings 310, 320 so that the scatter ratio may be measured at the center of the detector fans.

Although scatter ratio is measured only in the central detector elements behind the bar 420, the central detector elements behind the bar 420 are typically the detector elements where the primary x-rays 318 are most attenuated by the subject 20. Thus, the region behind the bar 420 is the region where accuracy of calibration is more important. The scale factor between detector rings 310 and 320 is then the ratio of the signals measured behind the bar 420 in detector rings 310 and 320.

In one embodiment, equal numbers of detector elements are located at the same azimuthal positions in both detector rings 310 and 320. To determine the scatter in detector ring 320 from subject 20 in single slice mode, a calibration scan is first taken of the phantom 400 in single slice mode. Detector elements near the center of each detector fan that are shadowed from primary x-rays 318 by the bar 420 contain only signal from scattered x-rays 319. The signal from scattered x-rays 319 measured in detector ring 310 may be labeled M1, and M2 may be the corresponding scatter signal measured in detector ring 320. For each detector element, the following expression may be used to estimate the scatter in detector ring 320 in single slice mode:

$$S2 = S1*M2/M1 \quad (1)$$

In equation (1), S1 is the signal measured in detector ring 310 during the single slice scan of the subject 20. S1 represents a measurement of the scatter from the subject 20. S2 represents a scaled scatter correction. The scaled scatter correction S2 is subtracted from the image data obtained in detector ring 320 during single slice mode. M1 and M2 represent average values of the scatter signal measured behind the bar 420 for the detector element. S1 and S2 are determined independently for each sample in the detector fan.

In dual slice mode, the collimation is adjusted so that both detector rings 310 and 320 are illuminated by primary x-rays 318 at the same time. To perform a scatter correction to dual slice data, an additional calibration is performed where data is taken with the phantom 400 in dual slice mode. Also, an additional scan of the subject 20 is obtained in single slice mode, although this scan may be a low exposure scan with a radiation dose perhaps comparable to the preview scan. The signal from scattered x-rays 319 measured in detector ring 310 in dual slice mode may be represented as n1, and n2 may be the corresponding scatter signal measured in detector ring 320. For each detector element, the following expressions may be used to determine the scatter corrections d1 for detector ring 310 and d2 for detector ring 320:

$$d1 = S1*n1/M1, \quad (2)$$

$$d2 = S1*n2/M1. \quad (3)$$

As in Equation (1), M1 is the signal measured in detector ring 310 during the calibration scan of the phantom 400 in single slice mode. The scatter signal S1 from detector ring 310 is measured in the separate scan of the subject 20 in single slice mode.

A single slice mode scan of the subject 20 to obtain scatter data in detector ring 310 may be performed with much less radiation exposure to the subject 20 than a full scan. For example, if 8 ms scans are performed on one-fifth of the total number of levels in the scan series, the additional radiation exposure equal to approximately 3.2% of the full scan series is comparable to the additional radiation exposure of about 3.9% from a preview scan performed routinely to position the subject 20 relative to the detector rings 310, 320. The scans for the scatter measurement of the subject 20 may be interspersed during a preview scan performed in single slice mode so that one full 8 ms sweep is completed after every five preview sweeps. A preview sweep is a small fraction of a full sweep and may not provide enough information for the scatter subtraction. For electron beam angiography, data from a single slice coronary calcium scan that is performed routinely before the dual slice angiography may also be used to obtain scatter data.

During the preview scan, the collimator is adjusted so that the primary x-rays 318, or x-rays generated from the electron beam 12 striking the target 14, are blocked from striking the detector ring 310. Thus, the detector ring 320 receives data from impacting primary x-rays 18 from the target 14. The detector ring 310 receives scatter x-rays 319 created by the subject 20 and by surfaces of system 8 components. Preferably, the detector ring 310 is closer to the electron source 32 than the detector ring 320. While preview scans are obtained in single slice mode with detector ring 310 receiving only scatter x-rays 319 and detector ring 320 receiving primary x-rays 318 plus scatter x-rays 319, full image scans may be executed in either single slice mode or in dual slice mode with both detector rings 310, 320 obtaining scatter data plus image data.

After the scans have been completed and image and scatter data obtained, the scatter data is scaled by the processor or computer subsystem 24 according to the scatter scale factor described above in Equations (1), (2) and (3). Scaling the scatter data helps to account for the difference in acceptance between the occluded detector ring 310 and the exposed detector ring 320. After scatter correction is determined for a given detector fan in the detector array 300, the scatter correction is smoothed to help ensure that the subtraction of scatter data from obtained image data varies smoothly within the same detector fan of data. Smoothing the scatter correction helps to prevent the introduction of image artifacts during scatter subtraction. In an embodiment, the scatter correction is smoothed by filtering the scatter correction using a Gaussian convolution filter. In a certain embodiment, scatter data is not smoothed between detector fans because detector element gains may vary.

A full image scan series may be executed to obtain image data from the subject 20. The subject 20 is first positioned using configuration information obtained from the preview scans. Image scans are performed using higher x-ray radiation dosages than the preview scans. While the preview scan typically sweeps only a portion of the subject 20, the image scan may sweep the entire subject 20. A full image scan is preferably a 50 ms sweep of the subject 20. In single slice mode, the detector ring 320 receives image data from x-rays (both scatter and primary) impinging upon detector elements of the detector ring 320. In dual slice mode, detector rings 310, 320 receive image data from x-rays impinging upon detector elements of the detector rings 310, 320.

After image data has been obtained, the scaled, smoothed scatter data is subtracted from the image data for each detector fan corresponding to a detector element in either detector ring 320 or detector ring 310 (for dual slice mode). The scatter correction may overestimate the actual scatter, particularly in a region away from the center of the detector fan where the scatter is not measured. Streaks may occur in the final image if the scatter estimate exceeds the raw data. Even in a region where the scatter is well measured, statistical fluctuations in the raw data may cause the scatter estimate to occasionally exceed the raw data and thereby create streaks in the image. Experimentally, it has been found that reducing the scatter correction by a factor of 0.7 in detector ring 320 (and 0.9 in ring 310 for the case of a dual slice correction) before the scatter correction is subtracted from the image data avoids streaks in the final image and effectively reduces artifacts from scatter.

After the image data has been corrected for scatter, the computer subsystem 24 may further process the image data for output and/or storage as an image. Image artifacts produced by scatter x-rays 319 are minimized in the resulting image. The image may be displayed on a monitor, printed, transmitted, and/or stored in a memory, for example.

Thus, certain embodiments of the present invention measure total x-ray scatter (machine scatter and object scatter) directly from the subject 20, such as a patient, at the center of each detector fan in the detector array 300 with no assumptions. Direct scatter measurement provides a significant improvement in scatter correction and minimizes scatter artifacts in resulting CT images.

Figure 5:
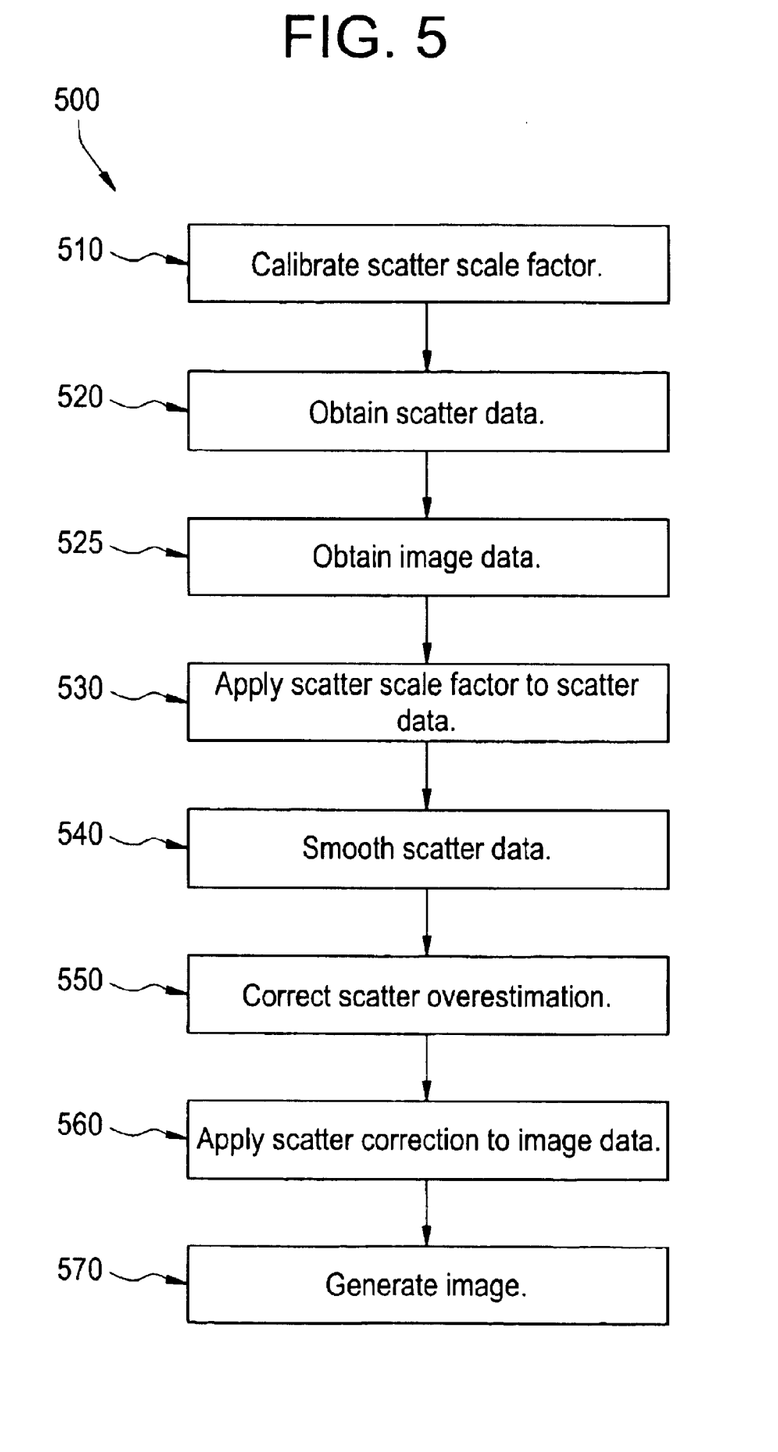
FIG. 5 illustrates a flow diagram for a method for scatter measurement used in accordance with an embodiment of the present invention.

FIG. 5 illustrates a flow diagram 500 for a method for scatter measurement used in accordance with an embodiment of the present invention. First, at step 510, calibration is performed to determine a scatter scale factor, for example the ratio M2/M1 in Equation (1). As described above in relation to FIG. 4, a phantom 400 is used to block primary x-rays 318 and measure scatter x-rays 319 at the detector rings 310 and 320 and then determine a ratio between the scatter measurements at each detector ring 310, 320. Scale factors for detector rings 310, 320 are determined according to equations (1), (2), and (3) described above.

For example, suppose that M1=102 counts and M2=173 counts for a measurement obtained behind a lead bar in an object scatter phantom in single slice mode. For a single slice scatter measurement using a G.E. Medical Systems phantom, S1=105, for example. The single slice data for the sample in detector ring 320 is 1854, for example. Thus, for single slice mode, scaled scatter correction S2=105*(173/102)=178. For the same measurement in dual slice mode, n1=102 and n2=128, for example. For dual slice scatter measurement, the data for the sample was 931 in detector ring 310 and 847 in detector ring 320, for example. Therefore, the scatter correction d1=105*(102/102)=105 and d2=105*(128/102)=131.765.

Next, at step 520, scatter data is obtained. As described above in relation to FIGS. 1, 2, and 3, scatter data may be obtained by interspersing 8 ms sweeps during the preview scan using detector rings 310, 320. The detector ring 310 is blocked or occluded from the primary x-rays 318 produced by the target 14 and, thus, receives x-rays scattered from the components of the system 8 or the subject 20. The detector ring 320 receives the primary x-rays 318 plus scatter x-rays 319. In a certain embodiment, a full image scan is performed for every five preview scans executed to obtain scatter data. Scatter data scale factors are calculated accordingly, as described above.

Then, at step 525, image data is obtained from a full image scan. The image data may be obtained for a single detector ring 320 or multiple detector rings 310, 320. The subject 20 is positioned based on configuration information obtained from the preview scan. Image data obtained in the scan includes image data from primary x-rays 318 irradiating the subject 20 and scatter x-rays 319 from the subject 20 and system 8.

At step 530, the scatter scale factor (or factors in the case of multiple slice imaging) is applied to the scatter data obtained from the detector ring 310 in step 520. Next, at step 540, the scaled scatter data is smoothed by convolving the scaled scatter data with a Gaussian kernel, for example, to help ensure that the subtraction of scatter data from obtained image data varies smoothly within the same detector fan. At step 550, an overestimation factor (such as 0.7, 0.8, or 0.9) is applied to the scatter correction data to minimize image artifacts induced by excess scatter correction.

Then, at step 560, the scatter correction is applied to the image data obtained in step 525. The scatter correction may be applied to image data from the detector ring 320 (single slice mode) or to image data from both the detector rings 310 and 320 (dual slice mode).

Finally, at step 570, an image is generated from the corrected image data. The image may be stored in a memory or other storage or may be output to a display, printer, or facsimile, for example. The resulting image may be used for medical diagnosis, treatment, or other such application.

Thus, certain embodiments of the present invention use dual ring geometry to measure x-ray scatter directly from the subject 20 with a small increase in total x-ray exposure to the subject 20. Scatter determination during a single slice scan allows scatter correction with reduced assumptions regarding scatter data and reduced x-ray exposure from an additional scan. An improved scatter correction results in improved image quality with fewer scatter artifacts. Improved image quality may have important diagnostic implications, such as in CT images of a heart during electron beam angiography with a contrast agent.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for scatter measurement and correction in a diagnostic imaging system, said method comprising:
   performing a calibration scan using a phantom to measure a scatter signal ratio between scatter x-rays impacting a first detector ring and scatter x-rays impacting a second detector ring, said scatter signal ratio used to determine a scatter scale factor;
   positioning a collimator such that said first detector ring is occluded from a path of primary x-rays generated by a target;
   executing a low exposure scan to obtain x-ray scatter data using said first detector ring;
   applying said scatter scale factor to said scatter data to produce sealed scatter data;
   obtaining image data using at least one of said first detector ring and said second detector ring; and
   adjusting said image data using said scaled scatter data.

2. The method of claim 1, wherein said phantom comprises a water-filled phantom said phantom including a bar in an interior portion of said phantom to block x-rays.

3. The method of claim 1, wherein image data is obtained during a 50 ms scan.

4. The method of claim 1, wherein said scaled scatter data is filtered using a Gaussian convolution filter.

5. The method of claim 1, wherein said scaled scatter data is further scaled for overestimation of x-ray scatter.

6. The method of claim 1, wherein said adjusting step comprises subtracting said scaled scatter data from said image data.

7. The method of claim 1, wherein said scatter data is obtained using a series of five low exposure scans and one full scan.

8. A diagnostic imaging system, said system comprising:
   first and second detector rings for detecting radiation, said first detector ring capable of being blocked from a primary path of said radiation, said first detector ring acquiring scatter data and at least one of said first detector ring and said second detector ring acquiring image data;
   an object scatter phantom for use in calibration of a scatter scaling factor for radiation scatter; and
   a processor for reducing scatter in said image data, said processor applying said scatter scaling factor to said scatter data, said processor subtracting said scatter data from said image data.

9. The system of claim 8, further comprising a collimator for controlling said primary path of said radiation.

10. The system of claim 8, wherein said object scatter phantom includes a boundary around an exterior of said phantom, an interior portion of said phantom filled with water, a bar positioned in said interior portion of said phantom to block radiation.

11. The system of claim 8, further comprising a filter for smoothing said scatter data.

12. The system of claim 8, wherein said first and second detector rings comprise a plurality of detector elements for receiving said radiation.

13. The system of claim 8, wherein said rust end second detector rings acquire said scatter data from a low exposure scan.

14. The system of claim 8, wherein said first and second detector rings obtain said scatter data using a series of five low exposure preview scans and one full scan.

15. A method for empirical scatter measurement, said method comprising:
   performing a calibration scan using an object scatter phantom to measure a scatter signal ratio between scatter x-rays impacting a first detector ring and scatter x-rays impacting a second detector ring, said scatter signal ratio used to determine a scatter scale factor;
   positioning said first detector ring such that said first detector ring is outside said primary path of said incoming radiation; and
   executing a preview scan to obtain positioning data regarding said first and second detector rings and a primary path of incoming radiation; and
   acquiring scatter data from said first detector ring.

16. The method of claim 15, further comprising applying said scatter scale factor to said scatter data.

17. The method of claim 15, further comprising filtering said scatter data to smooth said scatter data.

18. The method of claim 15, further comprising forming said primary path of said incoming radiation using a collimator.

19. The method of claim 15, further comprising positioning at least one of said first detector ring and said second detector ring to acquire image data.

20. The method of claim 19, further comprising adjusting said image data using said scatter data.

21. The method of claim 19, wherein said scatter data is acquired using a single slice coronary calcium scan.

* * * * *

UNITED STATES PATENT AND TRADEMARK OFFICE
CERTIFICATE OF CORRECTION

PATENT NO. : 6,789,943 B2
DATED : September 14, 2004
INVENTOR(S) : Geordie Henry Zapalac It is certified that error appears in the above-identified patent and that said Letters Patent is hereby corrected as shown below:

Column 10,
Line 34, delete "rust end" and substitute therefore -- first and --.

Signed and Sealed this

First Day of February, 2005

JON W. DUDAS
*Director of the United States Patent and Trademark Office*